US006066162A

United States Patent [19]

Hudson

[11] Patent Number: 6,066,162

[45] Date of Patent: May 23, 2000

[54] PACIFIER WITH RETRACTABLE NIPPLE

[76] Inventor: Cartresa Hudson, 743 Leamington, Wilmette, Ill. 60091

[21] Appl. No.: 09/183,131

[22] Filed: Oct. 30, 1998

[51] Int. Cl.[7] .......... A61B 17/00

[52] U.S. Cl. .......... 606/234

[58] Field of Search .......... 606/234, 235, 606/236; 215/11.1–11.6

[56] References Cited

U.S. PATENT DOCUMENTS

| | | | |
|---|---|---|---|
| 3,363,630 | 1/1968 | Hines . | |
| 4,878,496 | 11/1989 | Chen . | |
| 5,197,974 | 3/1993 | Scarpelli et al. | 606/235 |
| 5,366,481 | 11/1994 | Zade | 606/236 |
| 5,431,680 | 7/1995 | Jones | 606/236 |
| 5,578,058 | 11/1996 | Chen | 606/236 |
| 5,662,684 | 9/1997 | Caso | 606/234 |

*Primary Examiner*—Michael Buiz
*Assistant Examiner*—Vikki Trinh
*Attorney, Agent, or Firm*—Joseph N. Breaux

[57] ABSTRACT

A pacifier with retractable nipple wherein the nipple is retractable into the pacifier when the pacifier is not in use. The pacifier includes a pacifier body; a resilient, flexible nipple structure attached to the top edge of the pacifier body portion; and a retraction mechanism mechanically connected to a nipple tip portion of the nipple structure for mechanically inverting the nipple tip portion and pulling it within a compartment formed within the pacifier.

1 Claim, 2 Drawing Sheets

PACIFIER WITH RETRACTABLE NIPPLE

TECHNICAL FIELD

The present invention relates to baby pacifiers and the like and more particularly to a pacifier with a retractable nipple that includes a pacifier body portion having a bottom body portion opening; a resilient, flexible nipple structure attached to the top edge of the pacifier body portion; and a retraction mechanism mechanically connected to a nipple tip portion of the nipple structure for mechanically inverting the nipple tip portion and pulling it within a compartment formed within the pacifier; the nipple tip portion having a nipple tip attachment hook extending from an interior surface thereof; the retraction mechanism including a retraction rod having an open loop end mechanically connected to the nipple tip attachment hook, a ring shaped moveable handle attached to the opposite end of the retraction rod, a cone shaped extension stop portion formed on the retraction rod near the ring shaped handle and tapered toward the open loop end of the retraction rod, a cone shaped retraction stop portion formed on the retraction rod near the open loop end and tapered toward the ring shaped moveable handle, and a resilient position locking ring affixed along the perimeter edge thereof to an interior surface of the pacifier body portion and having a retraction rod passageway formed therethrough through which a central portion of the retraction rod between the cone shaped extension stop portion and the cone shaped retraction stop portion is slidably positioned; the retraction rod passageway having a diameter less than the largest ends of the cone shaped extension stop portion and the cone shaped retraction stop portion such that the when the cone shaped extension stop portion and the cone shaped retraction stop portion are force tapered end first, respectively, into the retraction rod passageway the resilient position locking ring expands and grips the respective cone shaped retraction stop portion and cone shaped extension stop portion; a bottom section of the retraction rod located between the cone shaped extension stop portion and the ring shaped moveable handle being slidably positioned through the bottom body portion opening.

BACKGROUND ART

Child care providers often use a pacifier to entertain and quiet infants. The pacifier typically includes a nipple that is inserted into the infant's mouth upon which the infant sucks. Although the pacifier pacifies and entertains the infant, the nipple can become contaminants with dirt, hair and the like when the pacifier is not being used. It would be a benefit, therefore, to have a pacifier that included a nipple that was retractable when not in use to prevent contamination of the nipple.

GENERAL SUMMARY DISCUSSION OF INVENTION

It is thus an object of the invention to provide a pacifier with retractable nipple wherein the nipple is retractable into the pacifier when the pacifier is not in use.

It is a further object of the invention to provide a pacifier with retractable nipple that includes a pacifier body portion having a bottom body portion opening; a resilient, flexible nipple structure attached to the top edge of the pacifier body portion; and a retraction mechanism mechanically connected to a nipple tip portion of the nipple structure for mechanically inverting the nipple tip portion and pulling it within a compartment formed within the pacifier; the nipple tip portion having a nipple tip attachment hook extending from an interior surface thereof; the retraction mechanism including a retraction rod having an open loop end mechanically connected to the nipple tip attachment hook, a ring shaped moveable handle attached to the opposite end of the retraction rod, a cone shaped extension stop portion formed on the retraction rod near the ring shaped handle and tapered toward the open loop end of the retraction rod, a cone shaped retraction stop portion formed on the retraction rod near the open loop end and tapered toward the ring shaped moveable handle, and a resilient position locking ring affixed along the perimeter edge thereof to an interior surface of the pacifier body portion and having a retraction rod passageway formed therethrough through which a central portion of the retraction rod between the cone shaped extension stop portion and the cone shaped retraction stop portion is slidably positioned; the retraction rod passageway having a diameter less than the largest ends of the cone shaped extension stop portion and the cone shaped retraction stop portion such that the when the cone shaped extension stop portion and the cone shaped retraction stop portion are force tapered end first, respectively, into the retraction rod passageway the resilient position locking ring expands and grips the respective cone shaped retraction stop portion and cone shaped extension stop portion; a bottom section of the retraction rod located between the cone shaped extension stop portion and the ring shaped moveable handle being slidably positioned through the bottom body portion opening.

It is a still further object of the invention to provide a pacifier with retractable nipple that accomplishes both of the above objects in combination.

Accordingly, a pacifier with retractable nipple is provided. The pacifier with retractable nipple includes a pacifier body portion having a bottom body portion opening; a resilient, flexible nipple structure attached to the top edge of the pacifier body portion; and a retraction mechanism mechanically connected to a nipple tip portion of the nipple structure for mechanically inverting the nipple tip portion and pulling it within a compartment formed within the pacifier; the nipple tip portion having a nipple tip attachment hook extending from an interior surface thereof; the retraction mechanism including a retraction rod having an open loop end mechanically connected to the nipple tip attachment hook, a ring shaped moveable handle attached to the opposite end of the retraction rod, a cone shaped extension stop portion formed on the retraction rod near the ring shaped handle and tapered toward the open loop end of the retraction rod, a cone shaped retraction stop portion formed on the retraction rod near the open loop end and tapered toward the ring shaped moveable handle, and a resilient position locking ring affixed along the perimeter edge thereof to an interior surface of the pacifier body portion and having a retraction rod passageway formed therethrough through which a central portion of the retraction rod between the cone shaped extension stop portion and the cone shaped retraction stop portion is slidably positioned; the retraction rod passageway having a diameter less than the largest ends of the cone shaped extension stop portion and the cone shaped retraction stop portion such that the when the cone shaped extension stop portion and the cone shaped retraction stop portion are force tapered end first, respectively, into the retraction rod passageway the resilient position locking ring expands and grips the respective cone shaped retraction stop portion and cone shaped extension stop portion; a bottom section of the retraction rod located between the cone shaped extension stop portion and the ring shaped moveable handle being slidably positioned through the bottom body portion opening.

BRIEF DESCRIPTION OF DRAWINGS

For a further understanding of the nature and objects of the present invention, reference should be had to the following detailed description, taken in conjunction with the accompanying drawings, in which like elements are given the same or analogous reference numbers and wherein.

EXEMPLARY MODE FOR CARRYING OUT THE INVENTION

Figure 1:
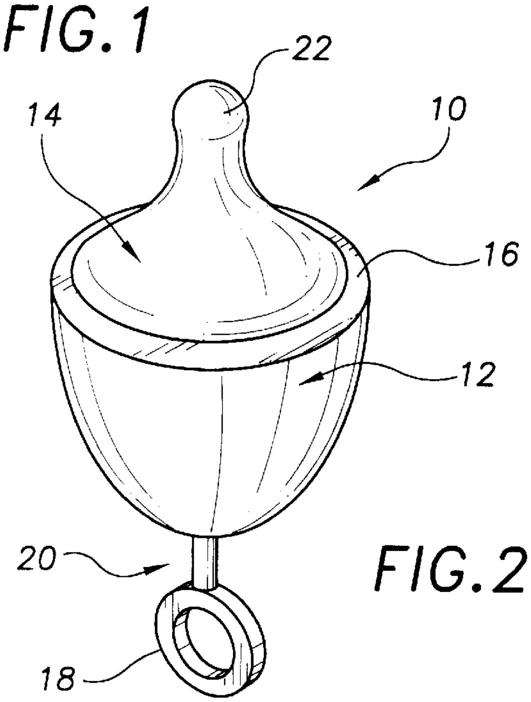
FIG. 1 is a perspective view of an exemplary embodiment of the pacifier with retractable nipple of the present invention showing the pacifier body portion; the resilient, flexible nipple structure attached to the top edge of the pacifier body portion; and the moveable ring shaped handle of the nipple retraction mechanism.

FIG. 1 shows an exemplary embodiment of the pacifier with retractable nipple of the present invention generally designated by the numeral 10. Pacifier with retractable nipple 10 includes a molded plastic pacifier body portion, generally designated 12; a resilient, flexibie latex nipple structure, generally designated 14, attached to a top edge 16 of pacifier body portion 12; and a moveable ring shaped handle 18 of a nipple retraction mechanism, generally designated 20, that is used to retract a nipple tip 22 of nipple structure 14 into pacifier 10.

Figure 2:
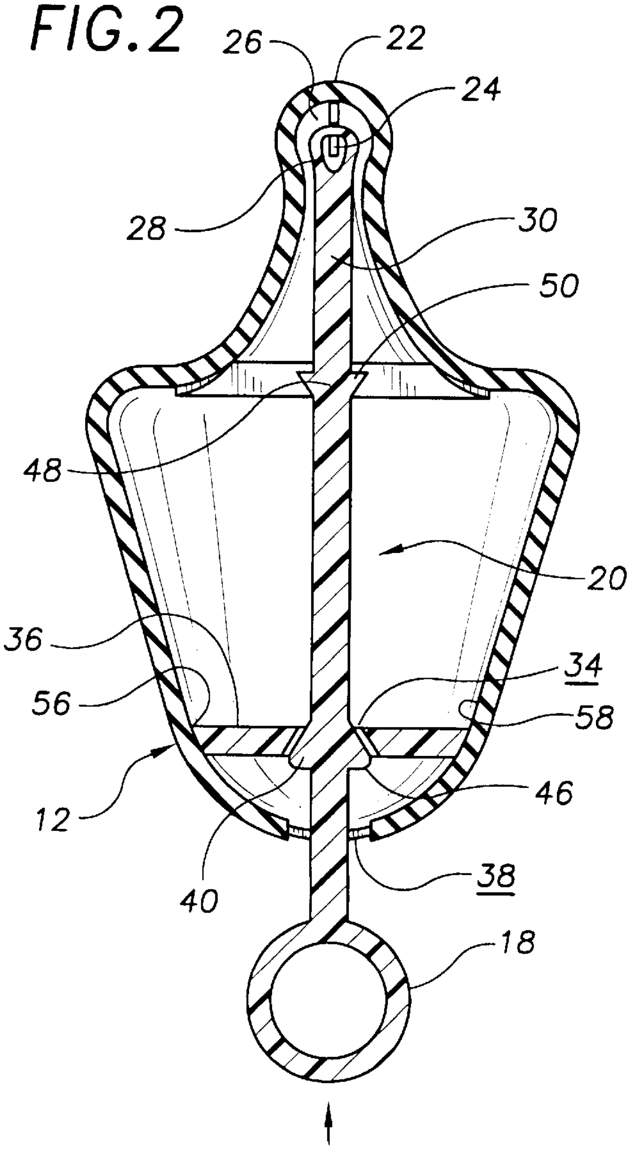
FIG. 2 is a sectional view of the exemplary pacifier with retractable nipple of FIG. 1 showing the nipple tip attachment look extending from an interior surface of the nipple tip and mechanically linked through the open loop end of the retraction rod of the retraction mechanism, the retraction rod extending between the nipple tip attachment hook and the ring shaped moveable handle and through the retraction rod passageway of the resilient position locking ring and the bottom opening of the pacifier body portion; a cone shaped extension stop portion formed on the retraction rod near the ring shaped moveable handle; and a cone shaped retraction stop portion formed on the retraction rod near the open loop end; each stop portion being sized larger than the retraction rod passageway of the resilient position locking ring; the perimeter edge of the resilient position locking ring being adhesively secured to the interior surface of the pacifier body portion.

Referring now to FIG. 2, a nipple tip attachment hook 24 extends from an interior surface 26 of nipple tip 22. Nipple tip attachment hook 24 mechanically links nipple tip 22 to an open loop end 28 of a retraction rod 30 that forms a portion of retraction mechanism 20. Retraction rod 30 is of molded plastic construction and extending between nipple tip attachment hook 24 and ring shaped moveable handle 18 and passing through a retraction rod passageway 34 (See also FIG. 4) of a resilient position locking ring 36 and a bottom opening 38 of pacifier body portion 12. A cone shaped extension stop portion 40 is formed on retraction rod 30 near ring shaped handle 18 and is tapered from a largest end 46 toward open loop end 28. A cone shaped retraction stop portion 48 is formed on retraction rod 30 near open loop end 28 and is tapered from a largest end 50 toward ring shaped moveable handle 18. Resilient position locking ring 36 is affixed along perimeter edge 56 thereof to an interior surface 58 of pacifier body portion 12.

Figure 3:
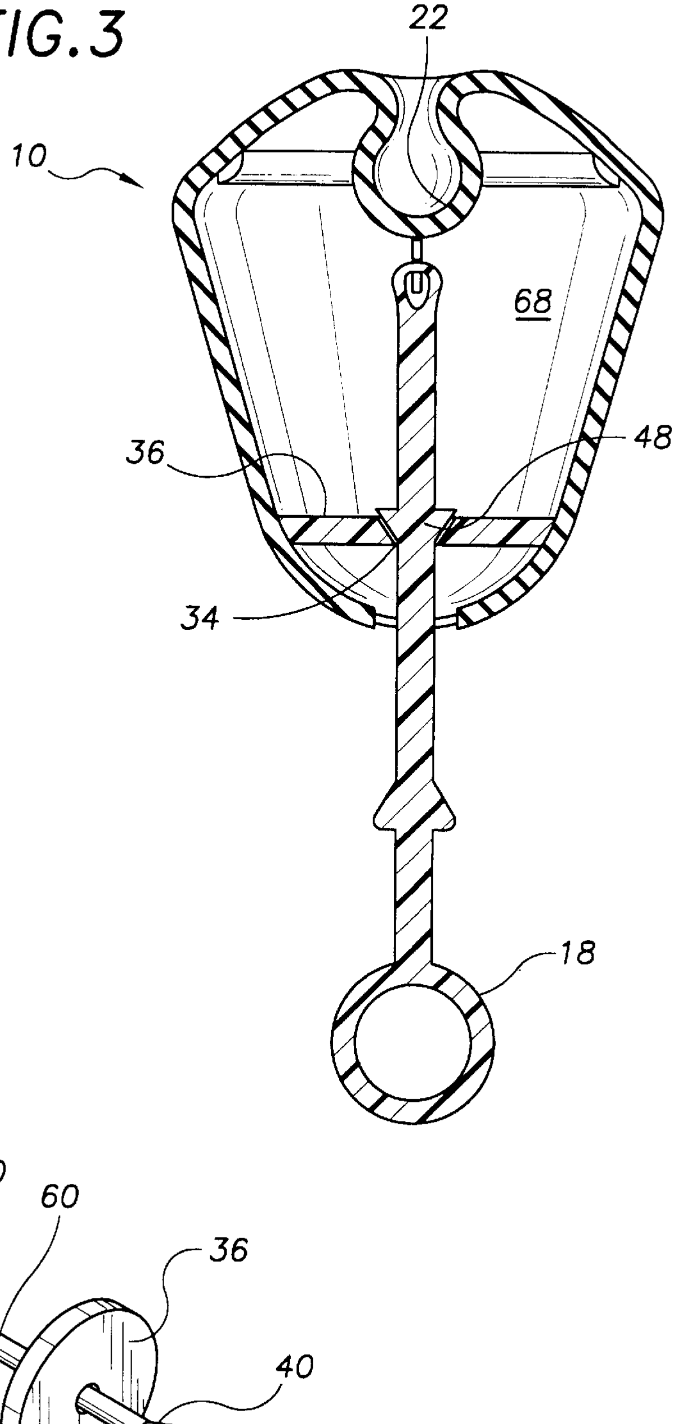
FIG. 3 is section view showing the nipple tip retracted and the cone shaped retraction stop portion resiliently lodged within the retraction rod passageway of the resilient position locking ring maintaining the nipple tip in the retracted position.
Figure 4:
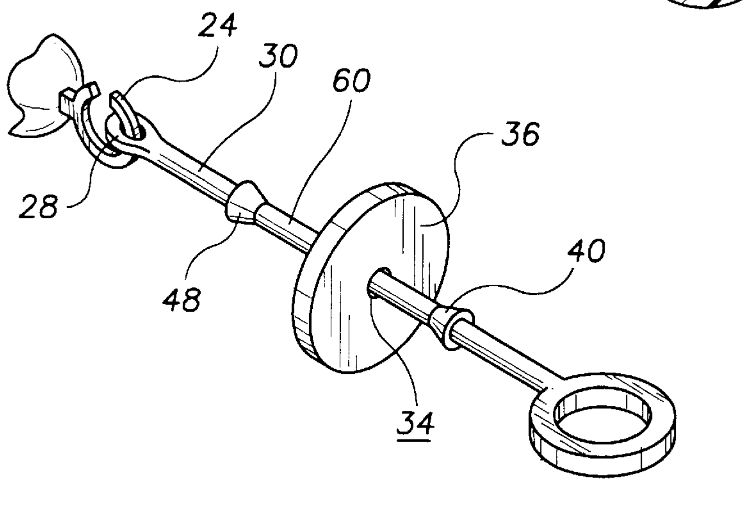
FIG. 4 is a perspective detail view showing the nipple tip attachment hook extending from an interior surface of the nipple tip and mechanically linked through the open loop end of the retraction rod of the retraction mechanism; the retraction rod extending between the nipple tip attachment hook and the ring shaped moveable handle and through the retraction rod passageway of the resilient position locking ring; the cone shaped extension stop portion tapered toward the open loop end of the retraction rod; and and the cone shaped retraction stop portion tapered toward the ring shaped moveable handle; the resilient position locking ring being positioned between the cone shaped extension stop portion and the cone shaped retraction stop portion.

Referring to FIG. 4, retraction rod 30 is positioned through retraction rod passageway 34 of resilient locking ring 36 such that resilient locking ring 36 is trapped along a central portion 60 of retraction rod 30 between cone shaped extension stop portion 40 and cone shaped retraction stop portion 48. Referring back to FIG. 2, nipple tip 22 is positioned into the extended position for use by pushing movable handle 18 toward pacifier body portion 12 until cone shaped extension stop portion 40 is forced into retraction rod passageway 34 and gripped by resilient locking ring 36. Referring now to FIG. 3, when it is desired to store pacifier 10 after use, nipple tip 22 is retracted into a compartment 68 formed within pacifier 10 by pulling ring shaped moveable handle 18 until cone shaped retraction stop portion 48 is forced into retraction rod passageway 34 and gripped by resilient locking ring 36. Nipple tip 22 is then protected from contamination by dirt, hair, and the like.

It can be seen from the preceding description that a pacifier with retractable nipple has been provided wherein the nipple is retractable into the pacifier when the pacifier is not in use; and that includes a pacifier body portion having a bottom body portion opening; a resilient, flexible nipple structure attached to the top edge of the pacifier body portion; and a retraction mechanism mechanically connected to a nipple tip portion of the nipple structure for mechanically inverting the nipple tip portion and pulling it within a compartment formed within the pacifier; the nipple tip portion having a nipple tip attachment hook extending from an interior surface thereof; the retraction mechanism including a retraction rod having an open loop end mechanically connected to the nipple tip attachment hook, a ring shaped moveable handle attached to the opposite end of the retraction rod, a cone shaped extension stop portion formed on the retraction rod near the ring shaped handle and tapered toward the open loop end of the retraction rod, a cone shaped retraction stop portion formed on the retraction rod near the open loop end and tapered toward the ring shaped moveable handle, and a resilient position locking ring affixed along the perimeter edge thereof to an interior surface of the pacifier body portion and having a retraction rod passageway formed therethrough through which a central portion of the retraction rod between the cone shaped extension stop portion and the cone shaped retraction stop portion is slidably positioned; the retraction rod passageway having a diameter less than the largest ends of the cone shaped extension stop portion and the cone shaped retraction stop portion such that the when the cone shaped extension stop portion and the cone shaped retraction stop portion are force tapered end first, respectively, into the retraction rod passageway the resilient position locking ring expands and grips the respective cone shaped retraction stop portion and cone shaped extension stop portion; a bottom section of the retraction rod located between the cone shaped extension stop portion and the ring shaped moveable handle being slidably positioned through the bottom body portion opening.

It is noted that the embodiment of the pacifier with retractable nipple described herein in detail for exemplary purposes is of course subject to many different variations in structure, design, application and methodology. Because many varying and different embodiments may be made within the scope of the inventive concept(s) herein taught, and because many modifications may be made in the embodiment herein detailed in accordance with the descriptive requirements of the law, it is to be understood that the details herein are to be interpreted as illustrative and not in a limiting sense.

What is claimed is:

1. A pacifier with retractable nipple comprising:

a pacifier body portion having a bottom body portion opening;

a resilient, flexible nipple structure attached to a top edge of said pacifier body portion and having a nipple tip portion; and a retraction mechanism mechanically connected to a nipple tip portion of said nipple structure for mechanically inverting said nipple tip portion and pulling it within a compartment formed within said pacifier;

said nipple tip portion having a nipple tip attachment hook extending from an interior surface thereof;

said retraction mechanism including a retraction rod having an open loop end mechanically connected to said nipple tip attachment hook, a ring shaped moveable handle attached to an opposite end of said retraction rod, a cone shaped extension stop portion formed on said retraction rod near said ring shaped handle and tapered from a largest end toward said open loop end of said retraction rod, a cone shaped retraction stop portion formed on said retraction rod near said open loop end and tapered from a largest end toward said ring shaped moveable handle, and a resilient position locking ring affixed along a perimeter edge thereof to an interior surface of said pacifier body portion and having a retraction rod passageway formed therethrough through which a central portion of said retraction rod between said cone shaped extension stop portion and said cone shaped retraction stop portion is slidably positioned;

said retraction rod passageway having a diameter less than said largest ends of said cone shaped extension stop portion and said cone shaped retraction stop portion such that when said cone shaped extension stop portion and said cone shaped retraction stop portion are forced, tapered end first, respectively, into said retraction rod passageway, said resilient position locking ring expands and grips said respective stop portion;

a bottom section of said retraction rod located between said cone shaped extension stop portion and said ring shaped moveable handle being slidably positioned through said bottom body portion opening.

* * * * *